United States Patent [19]

Greenwood et al.

[11] 4,034,743

[45] July 12, 1977

[54] AUTOMATED PULMONARY FUNCTION TESTING APPARATUS

[75] Inventors: James R. Greenwood, Friendswood; Philip M. Miller, Houston; Thomas S. Whitacre, Houston, all of Tex.

[73] Assignee: Airco, Inc., Montvale, N.J.

[21] Appl. No.: 625,791

[22] Filed: Oct. 24, 1975

[51] Int. Cl.² .......................................... A61B 5/08
[52] U.S. Cl. .............................. 128/2.08; 128/2.07
[58] Field of Search ....................... 128/2.07, 2.08

[56] References Cited

U.S. PATENT DOCUMENTS

| | | | |
|---|---|---|---|
| 3,621,835 | 11/1971 | Suzuki et al. | 128/2.08 |
| 3,726,270 | 4/1973 | Griffis et al. | 128/2.08 |
| 3,785,370 | 1/1974 | Richards et al. | 128/2.08 |
| 3,799,149 | 3/1974 | Rummel et al. | 128/2.07 |
| 3,818,901 | 6/1974 | Sanctuary et al. | 128/2.08 |
| 3,895,630 | 7/1975 | Bachman | 128/2.07 |
| 3,896,792 | 7/1975 | Vail et al. | 128/2.07 |

OTHER PUBLICATIONS

Hilberman; M., et al. *Journ. of Assoc. for Advanc. of Med. Instr.*, vol. 6, No. 1, Jan.–Feb., 1972, pp. 65–69.

*Primary Examiner*—Kyle L. Howell
*Attorney, Agent, or Firm*—David L. Rae; Larry R. Cassett; Edmund W. Bopp

[57] ABSTRACT

Automated pulmonary function testing apparatus includes a spirometer responsive to the breathing efforts of a patient for producing electrical signals which vary in accordance with volumes of breathed gas and central processing means for calculating one or more pulmonary function parameters associated with such volumes. Display means are adapted to visually display information supplied from the central processing means to an operator and/or a patient under test. In addition, keyboard means coupled to the central processing means are also provided such that upon operation of a particular key, tests may be selected and volumes or other calculated parameters may be visually displayed and/or printed on a permanent record medium.

2 Claims, 2 Drawing Figures

FIG. 2

AUTOMATED PULMONARY FUNCTION TESTING APPARATUS

BACKGROUND OF THE INVENTION

The present invention relates to apparatus for testing the pulmonary functions of a patient and more particularly to an interactive and fully automated pulmonary function testing system.

The testing of pulmonary functions of a patient is, many times, beneficial toward providing an understanding of a possibly diseased condition or other physical defects affecting a particular patient. Typically, pulmonary function testing is divided into three main areas. The first type of pulmonary testing is generally referred to as spirometry which provides measurements in terms of volume and breathing rates of different patient inspiratory and expirarory efforts. In addition, various flow rates at various stages of a test are also the type of data generated from spirometry testing. A second area of pulmonary testing is a set of procedure designed to determine the uniformity of the distribution of inspired air throughout the lungs of a patient. By virtue of such tests, pulmonary insufficiency can be determined even though the alveolor ventilation of a patient is normal. A third type of pulmonary testing concerns the ability of the lungs to diffuse inspired air through alveolar membranes and such tests provide an indication of the ability of the lung to arterialize venous blood by exchanging oxygen for carbon dioxide.

Although the foregoing areas of pulmonary function testing are widely known and have been practiced for many years, nonetheless, such testing has not developed results which are entirely satisfactory. For example, spirometry testing has conventionally utilized a recording chart or strip device adapted to be driven by a spirometer in response to various breathing efforts by a patient under examination. However, the data obtained from such testing is generally read by an operator from the graph inscribed upon the recording strip by observing certain maximum and minimum values thereon. Thus, ample opportunity for error and disparate results are, and have been, a chronic problem of pulmonary function testing equipment as many times it is only the visual observation of an operator which is relied upon to develop necessary data. In addition, by requiring that data be read from a recording strip or the like, the observation and recordation of such data is relatively time-consuming and thus reduces the ability of such systems to rapidly and accurately test a number of patients in a given period of time. Furthermore, it has been found that operators must possess significant levels of skill in order to operate conventional pulmonary testing equipment and must be carefully trained to enable proper interpretation of data developed by such devices.

A further serious deficiency of prior art pulmonary function testing equipment has been the general lack of interaction between the operator, the patient, and the testing apparatus. For example, in certain pulmonary function testing such as dynamic compliance tests, which will be described in greater detail hereafter, it is highly important in order to obtain valid data that the patient breathe at a constant rate of, for example, 30, 60 or 90 breaths per minute. Previously, the breathing rate of a patient was either monitored visually by an operator or assisted by means of a metronome or like device although neither technique effectively assured such constant breathing rates. Accordingly, an interactive testing system wherein such breathing rates are continually monitored during the acquisition of pressure and volume data necessary for such dynamic compliance tests such that necessary instructions for maintaining or altering a breathing rate may be displayed to a patient, is clearly a feature to be desired on pulmonary function testing equipment and which is a feature which has been lacking in prior art systems.

OBJECTS OF THE INVENTION

It is an object of the invention to provide improved pulmonary function testing apparatus.

It is a further object of the present invention to provide fully automated pulmonary function testing apparatus requiring relatively low levels of operator skill to obtain accurate pulmonary function information about a particular patient.

It is yet another object of the present invention to reduce differences in patient breathing effort caused by variances in operator commands, exhortations, etc.

It is yet another object of the present invention to provide automated pulmonary function testing apparatus including a central processing unit for enabling automatic and rapid calculation of various measurements concerned with such testing in response to data acquired during breathing efforts of a patient.

It is still a further object of the present invention to provide automated pulmonary function testing apparatus capable of accepting standard information relative to a typical patient and calculating therefrom normal values of pulmonary functions for subsequent comparison with corresponding values actually obtained from testing the pulmonary functions of a particular patient.

Other objects of the present invention will become apparent from the detailed description of an exemplary embodiment thereof which follows and the novel features of the present invention will be particularly pointed out in conjunction with the claims appended hereto.

In accordance with the broader aspects of the present invention, automated pulmonary function testing equipment includes means responsive to the breathing efforts of a patient for producing electrical signals varying in magnitude in accordance with volumes of breathed gas and central processing means for calculating one or more pulmonary parameters of said volumes. In addition, display means are adapted to visually display information supplied thereto to an operator and to a patient under test. Keyboard means having keys corresponding to such volumes and calculated parameters are provided such that upon operation of appropriate keys, tests may be selected and volumes or calculated parameters may be displayed.

Further in accordance with the present invention automated pulmonary function testing apparatus includes spirometer means for generating electrical signals in response to the volume of gas inspired by a patient under testing, central processing means connected to said spirometer means for calculating the actual breathing rate of said patient, means for generating electrical signals representative of a desired breathing rate, and means for comparing said electrical signals representative of actual and desired patient breathing rates and means for visually displaying to said patient the results of said comparison thereby indicating to said patient during a pulmonary function test whether the actual breathin rate is above or below a predetermined desired value. In addition, the automated pulmonary function testing apparatus in accordance with the invention comprises means for supplying signals to said calculating means representative of normal values of breathing volumes for a patient of a particular age height and sex, with said calculating means being effective to enable entry of the age, height and sex of the patient under test such that normal values of a person of th same age, height and sex as the patient under test may be calculated and compared with values actually obtained from testing a particular patient.

In the pulmonary function testing apparatus of the present invention, the electrical signals generated by a spirometer transducer, nitrogen, helium and carbon monoxide analyzers and a differential pressure transducer are fed through appropriate circuitry such as multiplexers and an analog-digital converter. In this manner, spirometry, distribution and diffusion data, respectively, is supplied to a data bus or conduit coupled to the converter output for transmission to a central processing unit. The output bus of this unit is connected through appropriate timing and control circuits to various output devices such as a patient cue display, operator display, printer and an X-Y-T plotting or recording device. In addition, the output bus is connected to the excitation circuitry of the spirometer to condition the same for operation in response to the breathing efforts of a patient under a particular ambient temperature. In addition to the central processing unit (C.P.U.), a read only memory is provided for storing sub-routines and instructions for operating the C.P.U. as well as for storing normal values. A read-write memory is also provided to enable storage of calculated values prior to the display thereof upon an operator display unit. Accordingly, necessary calculations are effected in the arithmetic unit of the C.P.U. under the control of stored sub-routines and instructions while such calculated results may be stored in the read-write memory prior to display thereof. In accordance with the foregoing, the present invention constitutes fully automated pulmonary function testing apparatus wherein spirometry data, distribution data and diffusion data are supplied in ordered fashion to a central processing unit, together with information representative of normal values of pulmonary functions of a person of equal age, height and sex as is the patient under test. Necessary calculations and comparisons are performed in a central processing unit and the results of such calculations and comparisons are displayed or supplied to particular output recording devices. In addition, a further important aspect of the present invention resides in the ability of the instant automated pulmonary function testing apparatus to monitor the breathing efforts of a patient under test and indicate to the patient whether such efforts are in accordance with predetermined desired breathing patterns.

BRIEF DESCRIPTION OF THE DRAWING

The invention will be more clearly understood by reference to the following detailed description of an exemplary embodiment thereof in conjunction with the following drawing in which.

DESCRIPTION OF PREFERRED EMBODIMENTS

Figure 1:
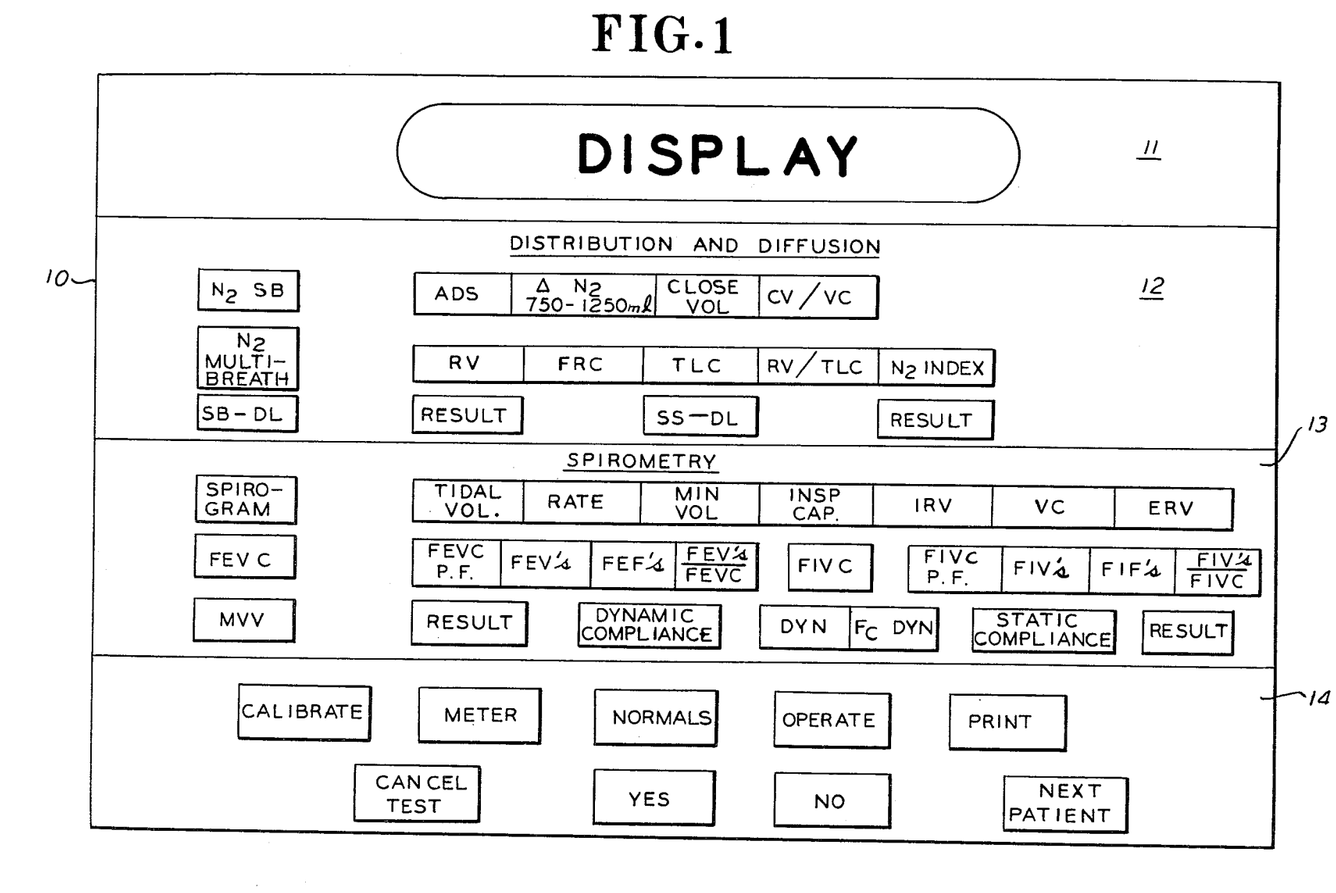
FIG. 1 is a diagrammatic view of a keyboard device utilized in connection with the automated pulmonary function testing apparatus of the present invention.

With reference now to FIG. 1, illustrated therein is an exemplary embodiment of a keyboard 10 generally comprised of display panel 11, distribution and diffusion panel 12, spirometry panel 13 and control panel 14. Display panel 11 preferably comprises a 32-character display element and may take the form of a known display device commercially available from Burroughs, Inc. under Model No. SSD 0132. Display panel 11 is preferably adapted in known manner to indicate both alphabetic and numeric characters such that pulmonary function test results as well as questions posed as a reminder to an operator will be visually displayed. Distribution and diffusion panel 12 is essentially comprised of a multiplicity of keys which are preferably adapted to enable an operator to select a particular distribution or diffusion test (to be described in greater detail hereafter) and to enable the display of results of such tests. A spirometry panel 13 and control panel 14 are provided with a plurality of keys for enabling spirometry tests and modes of operation to be selected, respectively. The distribution and diffusion tests, as well as spirometry tests, which will now be described are reported in detail in The Lung, Clinical, Physiology and Pulmonary Function Tests, Year Book Medical Publishers, Chicago, Illinois, 1971. However, in order to enable a full understanding of the automated pulmonary function testing apparatus in accordance with the present invention, such tests as may be conducted with an exemplary embodiment of this apparatus will be briefly described.

It has been recently found that in order to provide a complete evaluation of pulmonary functions, the uniformity of alveolar ventilation or the distribution of inspired gas throughout all areas of the lungs must be determined. One technique for providing numerical or quantitative indications of the distribution of inspired gas is known as the single breath nitrogen technique. In the course of this test, a patient inspires a single breath of pure oxygen and then expires slowly and evenly into a spirometer or flow meter while a nitrogen analyzer continuously records nitrogen concentration. Initially upon expiration, essentially pure oxygen which represents that inspired gas which remained in the airways between the patient's nose and lungs, will be expired and gradually the nitrogen concentration of expired gas will increase. For the first 750 ml. of expired gas, nitrogen concentration is not critical although over the next 500 ml. of expired or alveolar gas, the increase in nitrogen concentration is carefully monitored. It is considered that for a normal healthy person, the beginning and end (of the expired 500 ml.) of nitrogen concentrations would be substantially uniform and reflected as a horizontal line on an $N_2$ volume profile. However, if inspired oxygen is distributed unevenly throughout the lungs, the gas expired in the latter portion of this 500 ml. of expired gas will have a higher nitrogen concentration as this gas will come from those parts of the lung which receive little oxygen. Should such nitrogen concentration of expired gas increase substantially, such as by 10% or more, a poor distribution of expired gas throughout the lungs is indicated. In this manner, the single breath nitrogen technique reflects substantial changes in nitrogen concentration and thus is utilized to detect uneven distribution of inspired gas. The point of departure of nitrogen concentration, by way of an increase from the substantially constant level, can be utilized to calculate a "closing volume" within the last 500 ml. of expired gas. The larger the closing volume, the less evenly is inspired gas distributed throughout the lungs.

Referring now to distribution and diffusion panel 12, illustrated in FIG. 1, a key $N_2$ SB is provided to enable an operator to select a single breath nitrogen test. Upon conducting this test, several results will be automatically calculated and may be visually displayed upon operation of certain result keys. the key denominated A.D.S. (anatomical dead space) will be effective upon operation thereof to display, in numerical terms, the volume of expired gas containing a zero percent nitrogen content, or conversely, the volume of inspired gas which is not received by the lungs of the patient uner test and hence, the volume of the airways between the nose and lung of a patient under test. The second result key indicated as "$\Delta N_2 750-1250$ ml." is effective upon operation thereof to display the change in nitrogen concentration of expired gas over this critical 500 ml. volume. The third result key is preferably denominated as "close vol,". Upon operation of this key, the closing volume as heretofore defined will be visually displayed on panel 11 and will thereby provide a quantitative indication of the lack of uniformity of distribution of inspired gas throughout a patient's lung. The fourth result key which is denominated as "CV/VC" defines the ratio of closing volume to vital capacity, the latter term being defined as the total volume of gas expelled from a patient's lungs following maximum inspiration.

In a second distribution test, generally known as the $N_2$ multi-breath test, pure oxygen is inhaled for approximately 7 min. and the nitrogen concentration is monitored for each exhalation. Ideally, the nitrogen concentration in each breath of expired gas should continually decrease. However, if some areas of the lung are hypoventilated during normal breathing, a higher than ordinary $N_2$ concentration at the end of the 7 min. period will be present in expired gas. With reference to distribution and diffusion panel 12, a key denominated "$N_2$ multi-breath" is provided and upon depression thereof, the nitrogen concentration as detected by a nitrogen analyzer adapted to receive exhaled gas from a patient under test is monitored.

Further calculations from the results of the tests enable measuring, albeit indirectly, certain lung volumes which cannot be measured directly through conventional spirometry procedures. The residual volume (RV) is defined as the volume of gas in lungs at the end of maximal expiration and the functional residual capacity (FRC) is defined as the volume of gas in lungs at resting expiratory levels. Referring again to FIG. 1, and in particular to distribution and diffusion panel 12, a key denominated RV is provided such that upon depression thereof, the residual volume of a patient under test will be displayed on panel 11. Similarly, a key denominated FRC is also provided to enable display upon panel 11 of the functional residual capacity of a patient under test. It has been found that increases in the functional residual capacity can represent indications of hyperinflation during quiet breathing while increases in residual volume will provide a similar indication as well as altering an operator to the fact that a patient can not voluntarily force the lungs and thorax back to a normal size. This may indicate asthmatic conditions in younger people or emphysema or persistent bronchial obstructions in older people.

A further important volume to be determined in the course of pulmonary functions testing is total lung capacity (TLC) which is defined as the sum of the functional residual capacity and inspirator capacity (IC). The latter volume is defined as the maximal volume of gas that can be inspired from the resting expiratory level. Significant changes in total lung capacity can indicate extensive pulmonary disease. With reference again to distribution and diffusion panel 12, a key denominated TLC is provided to enable a display of total lung capacity upon depression thereof. A further key denominated RV/TLC is also provided to enable a display of the ratio of residual volume to total lung capacity. Finally, a key denominated $N_2$ INDEX is also provided. Upon depression of this key, the nitrogen concentration at the end of an initial tidal inspiration point will be monitored from a nitrogen analyzer and displayed upon panel 11 and is thus useful in the $N_2$ multibreath test.

Another dimension of pulmonary function testing is concerned with the ability of the lung to diffuse inspired gas through alveolar membranes and thereby measure the ability of the lungs to exchange oxygen for carbon dioxide. In a single breath test, a gas such as carbon monoxide which reflects a high depress of affinity for hemoglobin is inspired in a gas mixture having a relatively low, e.g. 0.3% CO concentration. The patient then holds this breath for approximately 10 seconds and the CO concentration of the gas expired after 10 seconds can be measured with the difference in CO concentration (of inspired and expired gas) thereby providing an indication of the diffusing capability of the alveoli. A measurement of the residual volume of a patient is necessary to calculate the CO uptake, as a value of the total alveolar volume during breath holding is required. This is accomplished by mixing the foregoing concentration of CO in a breathing gas containing a predetermined helium concentration, say 15% helium. The helium acts as a tracer gas and by sampling the helium concentration in and the volume of expired gas, residual volume may be calculated from the degree of helium dilution occuring in the patient's lungs. From residual volume, initial and final helium concentrations and supplied CO concentrations, the CO diffusion rate may be calculated. Referring again to FIG. 1, and to distribution and diffusion panel 12, a key denominated as SB-DL is provided for enabling single breath diffusion level testing. A key denominated RESULT is also provided such that upon depression thereof, the single breath diffusion level will be called up and displayed upon panel 11. A further type of diffusion testing generally known as the steady-state technique contemplates the breathing of a gas containing approximately 0.1-0.2% CO by a patient for approximately 12 breaths and the amount of CO transferred from the alveolar gas to capillary blood per min. is calculated by measuring CO in the inspired and expired gas and subtracting the latter from the former. This calculation yields a numerical indication of the diffusing capacity of the alveoli for carbon monoxide. A key denominated as SS-DL is provided on distribution and display panel 12 and a further key denominated RESULT is provided for enabling the calling up and display of the results of a steady-state carbon monoxide diffusion test.

In order to quantitatively determine various lung volumes, several spirometry tests which will be described hereinafter are conducted on a patient. With reference to FIG. 1, keyboard 10 is provided with a spirometry panel 13 which in turn includes a key denominated as SPIROGRAM. Upon depression of this key, a test for determination of various lung volumes may be conducted. One such volume to be determined is the tidal volume which is defined as the volume of gas inspired or expired during each normal respiratory cycle. Similarly, the rate of breathing may be calculated by measuring the time between peaks of tidal volumes and the minute volumes or the volume of gas inspired or expired per min. may be calculated by dividing tidal volume by the rate. Thus, in accordance with the present invention individual keys denominated as TIDAL VOL., RATE and MIN.VOL. are provided to enable a calculation and/or read-out of such volumes or rates and the display thereof on panel 11. Similarly, the inspiratory capacity and vital capacity of a patient is also capable of measurement by spirometric techniques and respective keys denominated as INSP. CAP. and VC are likewise provided to enable the reading and display of such parameters. Two further volumes capable to spirometry measurement are the inspiratory and expiratory reserve volumes with the former defined as the maximal amount of gas which can be inspired from the end-inspiratory position and the latter being the maximal volume of gas which can be expired from the end expiratory level. Individual keys denominated as IRV and ERV are provided on spirometry panel 13 such that upon depression thereof after a spirometric test, inspiratory and expiratory reserve volumes may be displayed or otherwise read from the pulmonary function testing system according to the present invention.

In order to monitor the mechanical ability of the lungs to inspire and expire, it has been found useful to monitor forced breathing efforts by a patient. As those patients with pulmonary disorders will generally show a marked decrease in inspiratory and expiratory efforts under maximal or forced conditions, such tests as will now be described are particularly helpful in diagnosing such defective conditions. The forced expiratory vital capacity, which is similar to vital capacity is defined as the maximum volume of gas expelled by force from the lungs following maximal inspiration. The term "forced expiratory volume" (FEV) refers to the volume of gas forcibly expired by a patient in a particular time period. Generally, the time period of interest ranges from 0.5–3 sec. and FEV's may be calculated for periods of 0.5, 1.0, 3.0 sec. The forced inspiratory vital capacity and forced inspiratory volumes are similar to forced expiratory vital capacity and FEV's although such relate to inspiration under maximal effort as opposed to similar expiration.

In order to provide for the recording and display of the forced expiratory vital capacity (FEVC) of a patient, a key denominated "FEVC" is provided. A further key denominated as FEVC P.F. is provided to enable the peak flow of FEVC to be called up and displayed. In addition, a key denominated as FEV's is also provided to enable calculation and display of forced expiratory volumes over predetermined time periods such as 0.5, 1.0 sec., etc. as mentioned heretofore. Similarly, forced expiratory flow rates may also be displayed upon depression of a key denominated as FEF's. Finally, a key denominated as FEV's/FEVC is provided to enable a determination of forced expiratory volumes at predetermined time intervals as a percentage of a forced expiratory vital capacity. Similar keys denominated as FIVC, FIVC P.F., FIV's, FIF's and FIV's/FIVC are also provided to enable calculation and display of similar parameters concerning the ability of a patient to inspire by maximal effort in terms of volume and flow rates. As noted heretofore, indications of pulmonary disorders will be easily indicated by comparison of actually obtained forced expiratory and inspiratory volumes and flows with similar volumes and flows of normal or healthy individuals.

A further spirometry test which is of assitance in determining muscular force available for breathing efforts and the resistance of airways and other passages is a test for the maximum voluntary ventilation. In this test, the maximum volume of gas that can be breathed per min. is determined. In a typical maximum voluntary ventilation test, the total inspired and expired gas volume is measured over a period of, for example, 15 sec. and from the measured volume, the minute volume may be calculated. In accordance with the present invention, a key denominated as MVV is provided such that upon depression thereof and subsequent appropriate inspiration and expiration by a patient, this test may be conducted. In addition, a RESULT key is also provided to enable a display or print-out of the results of such test upon conclusion thereof. A further mechanical test of the pulmonary capabilities of a patient is generally known as compliance testing which is defined in general as the volume change per unit of lung pressure change. The static compliance of lungs is related to pressure and volume while the dynamic compliance is related to the pressure differential required for a unit change of flow therethrough. Accordingly, a static compliance test is normally conducted against a closed shutter while a dynamic compliance test involves the patient breathing at a predetermined substantially constant rate such as 30, 60 or 90 breaths per min. Appropriate keys are provided on spirometry panel 13 of keyboard 10 to enable initiation of static and dynamic compliance testing. In addition, a key denominated as DYN and a key denominated as RESULT are provided such that upon depression thereof at the end of a corresponding compliance test, the results will be displayed on panel 11 or printed out as desired.

Keyboard 10 is additionally provided with a control panel which includes a plurality of keys each of which will now be briefly discussed. A CALIBRATE key is provided primarily for the purpose of enabling calibration of various gas analyzers, such as the helium, CO and $N_2$ analyzers utilized in the distribution and diffusion tests carried out in accordance with the automated pulmonary function testing system of the present invention. In essence, each of such gas analyzers is calibrated before any patients are tested and further calibration is usually not required. A key denominated METER is also provided merely for the purpose of providing internal voltages to predetermined locations of the apparatus to enable testing of various circuit components, printed circuit board connections and the like. The METER mode of operation thus is generally constricted to circuit testing functions. A further key denominated NORMALS is provided and operation of an exemplary embodiment of the apparatus in accordance with the present invention with a NORMALS mode will enable the display of the normal value of a parameter upon operation of a corresponding key. A further key denominated OPERATE is also provided such that upon depression thereof, any of the foregoing tests may be conducted. A PRINT key is also provided such that upon operation of a parameter or RESULT key and operation of the PRINT key, a printed record of the value of the parameter or result will be provided. In addition, operation of the PRINT key in a NORMALS mode will result in the printing of a complete table of normal values for a person of normal health of an age, height and sex corresponding to that of the patient under test. A pair of keys denominated as CANCEL TEST and NEXT PATIENT are also provided to enable the cancellation of a particular test or to effectively reset the apparatus in accordance with the present invention to a condition in which the next patient may be tested. Finally, keys denominated as YES and NO are provided to enable an operator to communicate with the automated pulmonary function testing system of the invention. For example, subsequent to a particular test, the operator may desired to display the normal value of a parameter or result obtained during the test as well as the percent of normal represented by this parameter or result. Upon operating the NORMALS key, the apparatus will be programmed to display a question to the operator such as "are normal values calculated"? Assuming such values have been calculated the operator will depress the YES key thereby enabling display of the appropriate normal value and percentage thereof represented by the result obtained from a particular corresponding test.

In summary, it will be understood that keyboard 10 is provided with a plurality of keys to determine the mode of operation of the automated pulmonary function testing system in accordance with the present invention with such mode keys being provided on control panel 14. In addition, a plurality of keys are provided for controlling distribution, diffusion and spirometry tests with corresponding keys also being provided to enable the display or other read-out of parameters obtained during such tests or, merely the results thereof. Thus, by merely depressing a particular key at the end of a given test, an operator will have either displayed or printed out the result of the tests and consquently, the time necessary for an operator to develop the results of tests conducted is substantially reduced. In addition, by removing the requirement of an operator to visually determine from graphical recordings various results and test measurements, the apparatus in accordance with the present invention now to be described in detail, effects an acquisition of more accurate pulmonary function testing data than heretofore possible.

Figure 2:
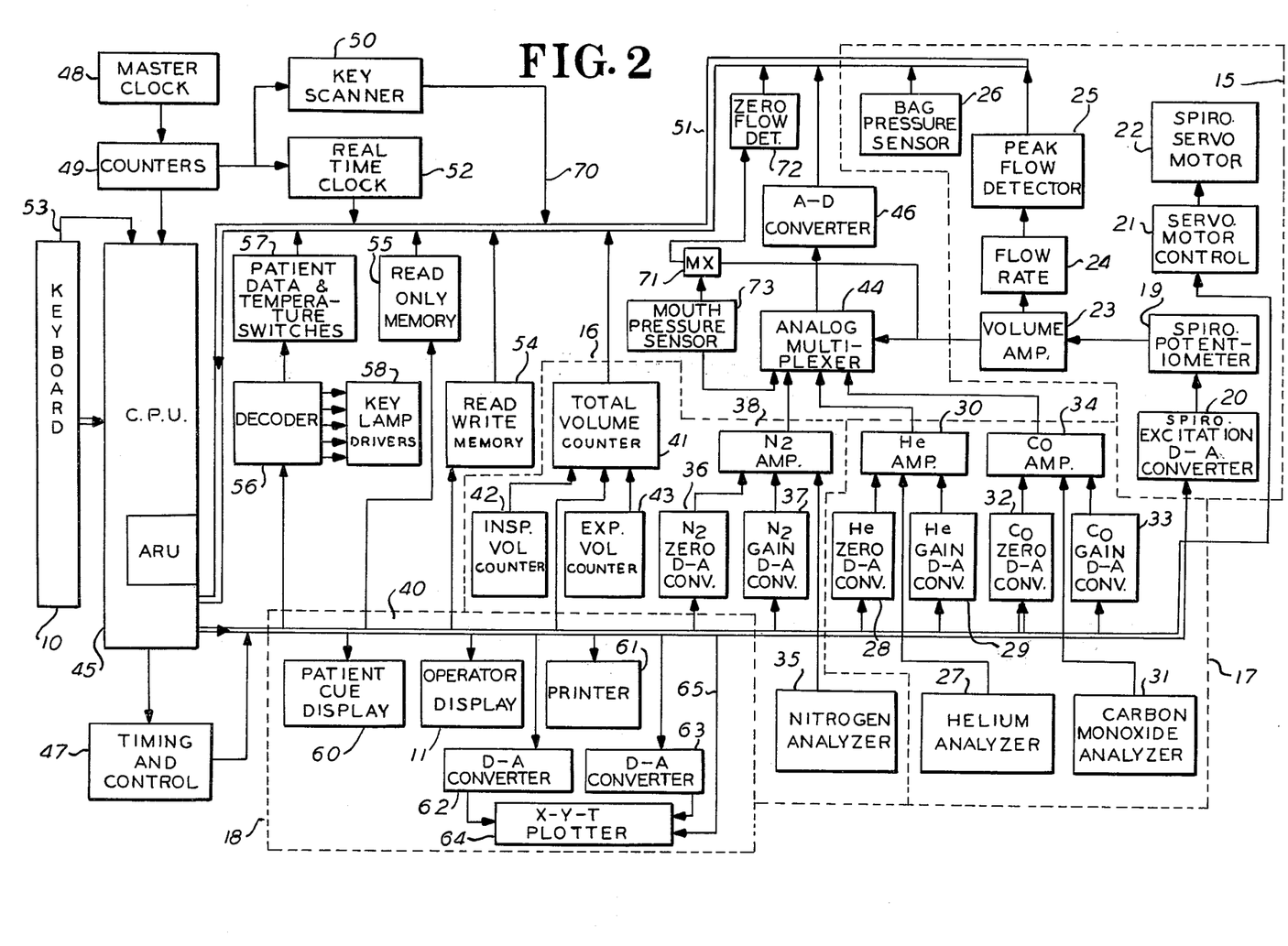
FIG. 2 is a block diagram of an exemplary embodiment of the automated pulmonary function testing system in accordance with the present invention.

Referring now to FIG. 2, illustrated therein is an exemplary embodiment of an automated pulmonary function testing system in accordance with the present invention which generally comprises a spirometry section 15, a distribution section 16, a diffusion testing section 17, a read-out and display section 18, a central processing unit (CPU 45) and associated clocking circuitry, memories and A-D and D-A converters. Spirometry section 15 is generally comprised of a spirometer potentiometer 19, spirometer excitation means 20, servo motor control 21, spirometer servo motor 22, volume amplifier 23, flow rate circuit 24, peak flow detector 25 and bag pressure sensor 26. Spirometry section 15 includes a spirometer which may comprise a conventional transducing apparatus for producing an electrical analog signal having an amplitude which varies in accordance with the volume of a gas breathed by a patient under test. For example, such a spirometery may comprise an apparatus commercially available from Ohio Medical Products, Madison, Wisconsin, under Model No. 842 and such apparatus will include a piston (not shown) which is linearly translatable in response to the aforementioned breathing efforts of a patient. Preferably, the movable contact of spirometer potentiometer 19 is affixed to the spirometer piston such that upon trnaslation thereof, an output voltage will be generated at such contact in correspondence to the linear translation of the piston. This output voltage constitutes an electrical representation of the volume of a gas either inspired or expired by a patient under test and this analog signal is supplied to volume amplifier 23 which may take the form of a conventional circuit adapted to increase the magnitude of an input signal supplied thereto. Spirometer excitation means 20 preferably comprises a digital to analog converter well known to those skilled in the art and is effective to supply a predetermined analog input voltage to spirometer potentiometer 19. It will be understood that as alveolar gas is normally at 37° C and the ambient temperature is considerably less, the volume of gas measured by a spirometer must be corrected for different water vapor partial pressures existing at the foregoing different temperatures. Accordingly, appropriate digital signals, which will be descirbed in greater detail hereafter, are supplied to spirometer excitation means 20 wherein such signals are converted to corresponding analog voltages subsequently supplied as the input potential to potentiometer 19.

Spirometer servo motor 22 which may take the form of a conventional servo motor is adapted to selectively drive the spirometer piston (not shown) in accordance with control signals applied thereto. More specifically, spirometer servo motor 22 is effective to set or adjust the initial position of the spirometer piston prior to commencing a spirometric test. For example, should it be desired to test the inspiratory capacity of a patient, the spirometer piston should be displaced sufficiently from an end position to enable the patient to effect the necessary inspiration. Servo motor control means 21 preferably comprises a pair of relays which are effective to selectively apply potentials of either polarity to servo motor 22 and to selectively control operation of a clutch (not shown) for engaging or disengaging servo motor 22. Typically, digital signals are supplied to servo motor control means 21 to engage the aforementiond clutch and drive servo motor 22 in the appropriate direction to enable the initial positioning of the spirometer piston. By monitoring the position of the spirometer piston by observing a graphical representation thereof on a suitable recording device, as will be described in greater detail hereafter, an operator may simply terminate operation of spirometer servo motor 22 and hence translation of the spirometer piston at a predetermined, desired location. The output of volume amplifier 23 is supplied as an input signal to flow rate circuit 24 which preferably comprises an electrical circuit well known to those skilled in the art and adapted to produce at the output thereof an electrical signal representative of the derivitative of the output of volume amplifier 23. Thus, flow rate circuit 24 may comprise a conventional differentiating circuit. Peak flow detector 25 is preferably comprised of a conventional up-counter which is effective to provide, in digital form, an output signal representative of the maximum or peak flow rate supplied as an input thereto from flow rate circuit 24. A bag pressure sensor 26, which preferably comprises a switching device is effective to generate a status signal indicating that a predetermined pressure has been reached in a pressure bag receiving gas expired by a patient. This status signal is utilized in diffusion tests and is supplied to CPU 45 over data bus 51. Mouth pressure sensor 73 which is coupled to multiplexers 44 and 71 is utilized to detect mouth pressures in compliance tests. For example, in static compliance testing, zero flow detector 72 may be utilized to indicate zero mouth pressure occurring at zero flow.

Distribution section 16 is generally comprised of nitrogen analyzer 35, digital-analog converters 36 and 37, amplifier and 38 and counters 41-43. Nitrogen analyzer 35 may take the form of any known device adapted to detect the concentration of nitrogen in a gas supplied thereto and produce an electrical output signal having a magnitude which varies in accordance with such nitrogen concentration. For example, analyzer 35 may comprise a nitrogen detecting apparatus commercially available from Ohio Medical Products under Model No. 720. The output of nitrogen analyzer 35 is supplied as an input signal to amplifier 38 which in turn is effective in known manner to increase the magnitude thereof and supply an amplified output signal to analog multiplexer 44. An $N_2$ zero digital-analog converter 36 and $N_2$ gain digital analog convertor 37 are adapted to supply appropriate analog output signals to nitrogen amplifier 38 in order to adjust the zero and gain thereof. Preferably, digital signals are supplied from CPU 45 over data bus 40 to converters 36 and 37 thereby enabling proper energization of $N_2$ amplifier 38 in a manner well known to those skilled in the art. In order to calculate certain pulmonary function distribution parameters, such as closing volume, it is necessary to measure certain volumes during operation of the apparatus in accordance with the present invention in a distribution, as opposed to spirometric, mode. Therefore, inspiratory and expiratory volume counters 42 and 43, respectively, which may comprise conventional vortex pneumotachs are provided. Preferably, each of counters 42 and 43 is provided with a rotatable vane mounted such that upon inspiratory or expiratory breathing efforts by a patient, rotation of the respective vane is effective to cause light interruptions to provide counts or pulses, each of which corresponds to a volume of 10 cc. of breathed gas. As each counter 42 and 43 operates unidirectionally, the output signal representative of the volume of gas breathed in either an inspiratory or expiratory period is selectively supplied as an input to total volume counter 41 which may comprise any known electrical counting circuit adapted to totalize pulses supplied thereto in a predetermined time period. At the end of each inspiratory and expiratory period of a pulmonary function test, the output of total volume counter 41 is supplied over input data bus 51 to CPU 45 which is also effective in known manner to reset counter 41. Accordingly, counters 41-43 are effective to generatedigital signals representative of the volume of either inspired or expired gas of a patient under test during corresponding inspiratory and expiratory periods.

Diffusion section 17 is preferably comprised of helium analyzer 27 carbon monoxide analyzer 31, digital-analog converters 28, 29, 32 and 33, and helium and CO amplifiers 38 and 34. Helium anlayzer 27, like nitrogen analyzer 35, is preferably comprised of a conventional device adapted to detect the helium concentration of a gas supplied thereto and is effective to provide an electrical signal corresponding to the magnitude of such concentration. Accordingly, the output of helium analyzer 27 is supplied as an input signal to amplifier 30 which is effective in known manner to increase the magnitude of the signals supplied thereto. Carbon monoxide analyzer 31 may comprise any device capable of receiving a gas and providing an electrical output signal representative of the carbon monoxide concentration of such gas. The output of CO amplifier 34 is supplied as an input signal to analog multiplexer 44. In addition, digital-analog converters 32 and 33 are effective to supply zero and gain control output signals to CO amplifier 34. Converters 32 and 33 are also supplied with appropriate digital signals from CPU 45 over output data bus 40 in known manner. Accordingly, diffusion level testing may be effected by means of section 17 wherein a gas containing, for example, 0.1-0.2% carbon monoxide, 15% helium, 20% oxygen and the balance nitrogen is supplied to a patient under test with the expired gas supplied to carbon monoxide analyzer 31 for an analysis of carbon monoxide in the expired gas in accordance with the single breath and steady-state diffusion level testing techniques previously mentioned.

With continued reference to FIG. 2, CPU 45 is provided with appropriate clocking and control circuitry as will now be described. A master clock 48, which may comprise a conventional pulse source preferably operable to provide an output signal at a frequency of 10mHz. is coupled to a set of counters 49 which may comprise a pair of conventional frequency dividing circuits effective to supply output pulses at a frequency of 1 mHz. or 100kHz. In addition, counters 49 include a known frequency dividing circuit which is effective to provide a clocking signal to CPU 45 at a frequency of approximately 500 k.H. Real time clock 52, which may take the form of a 4 decade counter which is coupled to the output of counters 49 and is configured such that at the higher frequency (1mHz.), the aforementioned 4 decade clock will be loaded in 10 ms. and at the lower frequency (100kHz.) clock 52 will be loaded in 100ms. Thus, real time clock 52 is effective to produce output signals every 10M. sec. or every 100m. sec. depending upon the frequency of the input signals supplied thereto. Key scanner 50 which may comprise a known oscillatormatrix encoder system for continuously scanning a plurality of keys, such as those keys provided with keyboard 10 as previously described, is supplied with an appropriate input signal of a frequency of 100 kHz. from counters 49. The output of key scanner 50 is coupled through input data bus 51 to CPU 45. Upon operation of CANCEL TEST or NEXT PATIENT key, an interrupt signal is supplied over line 53 to suspend operation of CPU 45 until the particular interrupt can be serviced. Upon scanning any other key except CANCEL TEST or NEXT PATIENT in an operated condition, a signal is supplied over line 70 to enable such instructions to be entered into and acted upn by CPU 45. As those skilled in the art will appreciate, key scanner 50 is effective to continuously scan the keys of keyboard 10 and, upon scanning an operated key, a code representative of this key is supplied at the output of scanner 50 and to CPU 45 via input data bus 51. Timing and control means 47, which may comprise conventional logic circuitry, is provided for the purpose of data to controlling and managing the supply of various sections of display module 18 which will now be described.

Module 18 generally comprises operator display 11, patient cue display 60, printer 61, D-A converters 62 and 63 and plotter 64. Operator display 11, which has been previously described in connection with the exemplary embodiment of keyboard 10 illustrated in FIG. 1, is illustrated in FIG. 2 for purposes of convenience as an element of display module 18. Patient cue display 60 which may take the form of a conventional 32 character display unit similar to operator display 11, is provided to visually display questions or instructions to a patient under test and is adapted to receive necessary data for such display from CPU 45 over output data bus 40. Printer 61 which may comprise a conventional printing device is also coupled to CPU 45 via output data bus 40 and is effective in known manner to produce a printed record to data supplied thereto. More particularly, in the course of operating the pulmonary function testing apparatus in accordance with the present invention in a print mode, the results of various distribution, diffusion and spirometry tests will be provided in the form of a permanent record by means of printer 60. Digital-analog converters 62 and 63 which may take the form of conventional devices for adjusting offsets, from zero, of analog signals along horizontal and vertical axes. Such analog signals comprise the inputs to multiplexer 44 and together with the output of flow rate circuit 24 are passed through a further multiplex (not shown), amplified and summed with the offsets generated by D-A converters 62 and 63 before being supplied to plotter 64. X-Y-T plotter 64, which may comprise a conventional graphical recording device is adapted to receive the aforementioned analog wave forms from converters 62 and 63 and is effective to produce a graphical representation of the aforementioned inspired and expired volumes of gas as a function of time. Preferably, suitable gating or logic circuitry (not shown) is provided in order to couple plotter 64 to CPU 45 by way of line 65 and output data bus 40.

Analog multiplexer 44 which may comprise a conventional circuit capable of accepting a plurality of input signals and providing the same as a plurality of time sequenced signals on a single output line is adapted to receive the output of volume amplifier 23, helium amplifier 30, CO amplifier 34 and N2 amplifier 38. The output of multiplexer 44 is connected to analog to digital converter 46 which may comprise known conversion circuitry adapted to receive an analog input and provide a digital output therefrom. Converter 46 is appropriately connected to input data bus 51 for supplying essentially all of the spirometry and diffusion data as well as a portion of the distribution data to CPU 45. As mentioned previously, the output of total volume counter 41 is supplied to CPU 45 via input data bus 51 and thus completes the circuitry required for acquiring and supplying plumonary function test data to CPU 45.

CPU 45 may take the form of an integrated circuit chip commercially available from Intel Corp. and may be conveniently provided along with associated driving circuitry on a single logic board. A READ-WRITE memory 54 which may comprise a conventional integrated circuit storage device is provided with an input connected to output data bus 40 and an output connected to input data bus 51. In operation, data in the form of test reresults or parameters calculated within the arithmetic unit of CPU 45 are stored in appropriate locations of READ-WRITE memory 54. Subsequently, upon depression of a particular result key by an operator, CPU 45 is effective to generate the appropriate address of such result in READ-WRITE memory 54 which is then effective to supply the same to input data bus 51 for display on operator display 11 or recording by printer 61 in dependence upon the particular mode of operation selected. A read only memory (ROM) 55 is similarly connected between output data bus 40 and input data bus 51. This memory is utilized for storage of subroutines and program instructions necessary to the operation of CPU 45 as well as for storage of variables associated with different pulmonary function parameters for patients of particular characteristics such as height, sex and age. Thus, in order to compare actual test results or parameters calculated with CPU 45 with normal values for an average patient, an appropriate calculation of such normal values is effected by CPU 45 and consequently, such normal values are available for comparison with the particular test result, or merely for display thereof an operator display 11.

A decoder 56 which may take the form of any known circuit capable of accepting a digitally encoded signal at an input thereof and producing an output at one of a plurality of output lines corresponding to said signal is provided with an input terminal connected to output data bus 40. Each of a plurality of output lines from decoder 56 are coupled to a set of key lamp drivers 58 each of which comprises a circuit for energizing a lamp adapted to illuminate a corresponding key of keyboard 10. Upon operation of a particular key by an operator, CPU 45 is effective to generate a code which is supplied to decoder 56 which in turn is effective to energize one of a plurality of output lines which output is connected to a lamp corresponding with the actual key depressed. In this manner, a key depressed by an operator is illuminated to thereby visually indicate the mode of operation effected or the test result or parameter selected to be read and displayed or printed.

Patient data and temperature switches 57 which may take the form of conventional manually operable dial switches are provided to enable information concerning the particular patient under test together with ambient data to be entered into CPU 45. As the normal value of parameters and results of pulmonary function testing will depend largely upon the age, height and sex of a patient, as well as upon ambient conditions, such information is supplied to CPU 45 to enable calculation of normal values upon request by an operator for such information. Accordingly, switches 57 will include a pair of dial selector switches for enabling entry of a patient's age in years, a further pair of switches for enabling entry of a patient's height in inches and a single switch for entering the patient's sex. In addition, further switches are provided for enabling entry of ambient temperature to CPU 45. The reason for requiring the entry of ambient temperature data will be understood when it is considered that the partial pressure of water vapor in air varies as a function of temperature. Furthermore, Boyle's law requires that for a given change in gas pressure, there is a change in volume according to the formula $P_1V_1 = P_2V_2$. As the temperature of air within a spirometer is normally on the order of 20°–25° C and the temperature within a patient's lungs is approximately 37° C, the volume of gas measured by the spirometer must be corrected for the difference in the partial pressure of water vapor existing in gas within a patient's lungs and gas within the spirometer. However, as water vapor partial pressures corresponding to temperatures between 20°–37° C are known, variables necessary for solving the above equation can be stored in tabular form in ROM 55. By appropriately programming CPU 45, such that the arithmetic unit thereof is effective to solve the foregoing equation according to Boyle's law, a correction factor to compensate for volume changes in accordance with Boyle's law can be generated and subsequently utilized in calculating normal values. The calculated corrected factor is then supplied by CPU 45 over data bus 40 to spirometer excitation D-A converter 20 to set the proper excitation of spirometer potentiometer 19. It should be noted that the reading of patient data and temperature switches 57 will be effected under the control of CPU 45 such that by supplying an appropriate code to decoder 56, the status of switches 57 will be read.

In addition to the foregoing structure essentially comprising the pulmonary function testing apparatus according to the present invention, a patient under test is provided with a single mouthpiece (not shown) which is selectively placed in communication with the spirometer (not shown), helium, CO and $N_2$ analyzers 27, 31, 35 respectively, or the inspiratory and expiratory volume counter depending upon the particular test to be conducted. In addition, different gases such as pure oxygen, or various gas mixtures such as a mixture including a small percentage of carbon monoxide, are also selectively supplied to a patient under test through such mouthpiece, again in dependence upon the particular test being conducted. In order to provide such gas or gas mixtures to a patient under test, a plurality of valve drivers (not shown) controlled by CPU 45 are provided to establish the necessary communication between the patient under test and respective sources of such gas or gas mixtures.

The operation of the plumonary function testing apparatus in accordance with the present invention will now be described with reference to the spirometric section 15, distribution section 16 and diffusion section 17. However, before describing such operations, it is noted that reference will be made to the performance of various calculations to obtain certain parameters and test results. Such calculations will be conducted in CPU 45 and in particular within the arithmetic unit thereof. However, as such calculations are generally known and may be found in the aforecited reference, The Lung, such calculations will only be described in detail to the extent necessary to fully set forth the operation of automated pulmonary function testing apparatus in accordance with the present invention. Before conducting any particular test, the aforementioned apparatus is appropriately electrically energized and analyzers 27, 31, and 35 are suitably claibrated. Necessary instruction and sub-routines governing the operation of CPU 45 are loaded in read only memory 55 together with variables associated with different pulmonary function parameters for individuals of different ages, heights and sex. Patient data and temperature switches 57 are appropriately set with the values established thereby read to CPU 45 which in turn is effective, upon operator request, to calculate appropriate normal values of parameters and results for the particular patient undergoing test. Normal values so calculated are then preferably stored in read-write memory 54. CPU 45 is also effective to generate signals and supply the same to spirometer excitation D-A converter 20 for appropriately energizing spirometer potentiometer 19. In addition, appropriate control signals are supplied by CPU 45 to servo motor 21 to initially adjust the position of the piston (not shown) thereof. The operator depresses a particular key to select a desired test and it may be desirable to flush the air within the spirometer before testing to avoid having the patient breath any stale air. Then, the operator is queried by way of operator display 11 to signify (by pressing a YES button) that plotter 64 is appropriately configured and ready to continue with the test. In addition, the patient is instructed by the patient cue display 60 as to the breathing pattern required for the selected test.

X-Y-T plotter 64 is subsequently energized and the patient is then connected to the spirometer which is now ready for testing. Assuming that, for example, tidal volume, rate and minute volume are to be tested, the patient is asked to breathe normally by virtue of a display of this instruction on patient cue display 60 and after a predetermined period of time, the patient may terminate such breathing effort. The volume of gas inspired and expired is detected by the spirometer which is effective to produce an electrical output signal at spirometer potentiometer 19 which in turn is supplied through volume amplifier 23 to analog multiplex 44 and A-D converter 46. In order to determine tidal volume, for example, certain points in the breathing cycle, such as peaks, are detected by passing the output of volume amplifier 23 through a multiplexer 71 and zero flow detector 72. The output of detector 72 is supplied to CPU 45 which "reads" the value of this peak temporarily held in converter 46. The value of this peak representing the tidal volume of breathed gas is stored in memory 54 and by obtaining a plurality of peak values, an averge volume corresponding to tidal volume and thus constituting the result of this test is also stored in memory 54. After the foregoing breathing cycles, the patient is asked via patient cue display 60 to breathe in a predetermined manner and the sequence of instructions and patient response is repeated until all necessary spirometric information is obtained.

The rate of breaths per minute is calculated within CPU 45 and the minute volume is then calculated by multiplying the volume detected by the breaths per minute. Other results of this test are calculated in a similar manner and stored for eventual recall in read write memory 54. Plotter 64 will depict a graphical representation of the spirogram test. By pressing a RESULT key denominated TIDAL VOLUME, this result will be read from memory 54 and displayed upon display panel 11. A second depression of this RESULT key will cause CPU 45 to calculate the normal value of tidal volume as described above. The normal value and the per cent thereof represented by the actual measured tidal volume will then be displayed upon operator display 11. It will be understood that this in test just described, for purposes of illustration, several parameters, one of which in TIDAL VOLUME were determined and several calculations have been rapidly and accurately made in connection with this parameter. Therefore, the operator is not required to visually attempt to read this parameter from plotter 64 but may rely upon a more accurate determination thereof as a consequence of operation of the automated pulmonary function testing apparatus of the present invention.

In a test for determining forced expiratory vital capacity, a patient expires breathed gas at a maximum effort as long as possible. The volume of such expired gas is translated into electrical signals of corresponding amplitude by spirometer potentiometer 19 with such signals being subsequently supplied through volume amplifier 23, analog multiplexer 44 and to A-D converter 46. In addition, the flow rate of such expired gas will be calculated by flow rate circuit 24 and supplied to peak flow detector 25. Converter 46 and detector 25 are subsequently read by CPU 45 which is effective to calculate the forced expiratory volumes in predetermined time intervals, e.g. 1.0 sec., 3.0 sec., etc. In addition, forced expiratory flows (FEF) are also calculated for similar time intervals as are the ratios of forced expiratory volumes (FEV's/FEVC). The results of such calculations and the data read from converter 46 and detector 25 are then passed to memory 54 for storage until the termination of this test whereupon such calculated and read values may be displayed by operation of appropriate keys of keyboard 10. Similar parameters and results are attained by monitoring the forced inspiratory vital capacity of a patient under test. In a test to determine the maximum voluntary ventilation (MVV), a patient breaths with maximal effort for a predetermined time interval, e.g. 10, 15 sec. and the volume of breathed gas is similarly converted to an electrical analog signal by spirometer potentiometer 19 which in turn is converted to a digital signal by A-D converter 46. This value is then read by CPU 45 which is operable to multiply the read value by an appropriate factor to determine MVV in terms of liters/min.

Referring now to the performance of distribution tests by a patient in conjunction with the automated pulmonary function testing apparatus of the present invention, and in particular to a single breath nitrogen test ($N_2$ SB), a patient inspires a full breath of pure oxygen and then expires at a substantially constant rate through nitrogen analyzer 35 and expiratory volume counter 43. The nitrogen concentration of expired gas is detected by analyzer 35 which is effective to supply an electrical analog signal representative of such concentration to $N_2$ amplifier 38 and subsequently to analog multiplexer 44 and A-D converter 46. Information representative of such nitrogen concentration is supplied over input data bus 51 to CPU 45 and separately to D-A converters 62 and 63 for recording on plotter 64 as previously described in connection with the recording of volume information. The volume of expired nitrogen is detected by expiratory volume counter 43 which in turn supplies an electrical signal to total volume counter 41. The volume of expired gas is subsequently supplied in digital form over input data bus 51 to CPU 45 wherein volume increments are stored at regular intervals of time. The aforementioned volume increments are then compared with a reference value to determine whether or not the patient expiration rate is above or below a predetermined desired rate. In the event that such comparison indicates that an increment of volume corresponding to such predetermined time interval is above a predetermined volume increment, patient cue display 60 may be enabled to instruct a patient by displaying a term such as "SLOWER" in order to advise the patient that the present breathing rate is above a predetermined value. Similarly, in the event that the measured time interval corresponding to such predetermined volume of expired gas is greater than a reference time interval, the patient cue display 60 is supplied with an appropriate signal from CPU 45 to instruct the patient to increase the rate of expiration in this single breath nitrogen test. Further, in the event that the patient is expiring gas at an acceptable rate, patient cue 60 supplied with a signal from CPU 45 to display "FLOW O.K." thereby advising the patient that the present rate of expiration is acceptable. In accordance with the foregoing, it will be appreciated that the automated pulmonary function testing apparatus according to the present invention enables a further degree of patient-apparatus interaction such that the breathing efforts of a patient can be accurately monitored thereby improving the reliability of pulmonary function test data obtained from a particular test, in this case a single breath nitrogen distribution test. Various parameters concerned with this test such as anatomical dead space, closing volume, etc. are calculated within the arithmetic unit of CPU 45 in accordance with the definitions of such parameters set forth hereinbefore.

In a typical $N_2$ multi-breath test, a patient begins breathing pure oxygen at a resting expiratory level, for example, with the total gas inspired and expired counted by means of counters 42 and 43. Accordingly, total volume counter 41 is effective to supply in digital form a signal indicative of the total volume of gas breathed during a period in which nitrogen within a patient's lung is "washed out". Normally, a patient breathing pure oxygen will effect such a nitrogen "wash out" in approximately 2.0 min. The nitrogen concentration of breathed gas in then detected by nitrogen analyzer 35 which is provided as an electrical signal through amplifier 38, multiplexer 44 and A-D converter 46. Upon reading total volume counter 41 and the converter 46, CPU 45 is operable to calculate the alveolar volume beginning from a resting expiratory level as the lung gas is known to have been 80% nitrogen at the commencement of this test. In this manner, functional residual capacity may be calculated and upon depression of a key denominated FRC, such result will be displayed on operator display 11. In addition, CPU 45 is effective to calculate residual volume (RV) by commencing such a $N_2$ multi-breath test at the maximum expiratory level. Consequently, total lung capacity (TLC) and the ratio of RV/TLC are also calculated and may be displayed by an operator depressing an appropriate key on panel 12 of keyboard 10 (FIG. 1).

In a single breath diffusion level test, referred to hereinbefore as a CO uptake test, a patient inspires a gas containing predetermined precentages of He and CO. After a predetermine period of time, say 10 seconds, the patient expires the inspired gas and final CO and He concentrations are detected by analyzers 31 and 27. The outputs of analyzers 27 and 31 are supplied as electrical analog signals to amplifiers 30 and 34 and subsequently to analog multiplexer 44 and A-D converter 46. The foregoing initial and final helium levels and the final CO level are read from converter 46 by CPU 45 wherein the CO diffusion rate is calculated. The value of this calculated diffusion rate is stored in memory 54 and upon depression of the appropriate key on panel 12, such value is displayed upon operator display panel 11.

As described above, when the apparatus according to the present invention is conditioned for an OPERATE mode, depression of a RESULT Key on termination of a test will cause the particular result to be displayed on operator display panel 11. Upon a second depression of the same RESULT key, the normal value and the per cent of normal represented by the actual value obtained during testing will be flashed upon display panel 11. In the event that further results for this test are avail the lamp illuminating this RESULT key will flash on and off. In this manner, the operator is advised that further results for this test, such as $FEV_{.5}$, $FEV_{1.0}$, etc, are available. By again depressing this key, results of the next test are displayed on panel 11 and by further depression of this key, normal values and the percent of normal represented by the actual value obtained will also be displayed. Finally, upon the lamp illuminating this RESULT key remaining in a steady state (non-flashing) condition, an indication that no further test results are available for this test is provided.

The present apparatus may be operated in a NORMALS mode. In this mode, the normal valve for a particular parameter or result will be displayed upon operator display panel 11 upon the depression of a particular RESULT key by an operator. In addition, should it be desired to obtain a printed record of NORMAL values, depression of the PRINT key on control panel 14 will result in a table of all normal values printed out by means of printer 61. Accordingly, the automated pulmonary function testing apparatus in accordance with the present invention enables rapid and accurate access to all normal values for a patient of a particular height, age and sex.

While the present invention has been particularly described in terms of specific embodiments thereof, it will be understood that numerous variations upon the invention are now enabled to those skilled in the art, which variations are again within the instant teachings. Accordingly, the present invention is to be broadly construed and limited only by the scope and spirit of the claims now appended hereto.

What is claimed is:

1. Automated pulmonary function testing apparatus comprising spirometer means responsive to the breathing efforts of a patient under test for producing electrical signals varying in magnitude in accordance with volumes of breathed gas, said spirometer means having a potentiometer to which an excitation signal is supplied, a central processing unit having an arithmetic unit therein; means for supplying digital representations of said electrical signals to said central processing unit for calculation in said arithmetic unit of one or more pulmonary function parameters; patient display means and operator display means both coupled to said central processing unit for visually displaying to the patient during a pulmonary function test instructions defining breathing efforts required of the patient, and for visually displaying the results of said test to said operator, respectively; keyboard means coupled to said central processing unit and having a plurality of test keys each of which corresponds to a particular pulmonary function test to be conducted and parameter key means associated with each of said test keys such that after a particular test is conducted, operation of said parameter key means enables calculation in said arithmetic unit, and display on said operator display means, of the parameter corresponding to said operated parameter key means, said keyboard means comprising means for supplying signals representing ambient temperature to said central processing unit for calculation in said arithmetic unit of spirometer potentiometer excitation signals corrected for difference between the water vapor partial pressure of (1) the exhaled breath of a patient under test and (2) the air in said spirometer means; and means for coupling said central processing unit to said spirometer potentiometer such that corrected excitation signals are supplied to said spirometer potentionmeter and subsequent correction of said electrical signals produced by said spirometer means for said difference in water partial pressure is rendered unnecessary.

2. Apparatus as defined in claim 1 wherein said spiromter means comprises a spirometer servo motor and servo motor control means coupled to said central processing means and to said spirometer servo motor for supplying signals to said servo motor effective to adjust the initial position of said spirometer prior to commencing pulmonary function testing of a patient.

* * * * *